United States Patent [19]

Owen

[11] 3,943,142
[45] Mar. 9, 1976

[54] DYE INTERMEDIATES AND THEIR PREPARATION AND USE IN THE SYNTHESIS OF METHINE DYES

[75] Inventor: John R. Owen, Rochester, N.Y.
[73] Assignee: Eastman Kodak Company, Rochester, N.Y.
[22] Filed: Jan. 24, 1969
[21] Appl. No.: 793,900

[52] U.S. Cl............ 260/298; 260/240 F; 260/240.4; 260/240.7; 260/240.9; 260/307 D; 260/309; 260/302 F
[51] Int. Cl.$^2$..................................... C07D 277/64
[58] Field of Search ..... 260/298, 302, 240.9, 240.4, 260/302 R, 302 F, 129 D, 307 D

[56] References Cited
UNITED STATES PATENTS
2,921,067  1/1960  Larive et al................. 260/240.65

OTHER PUBLICATIONS
Metzger et al., Bull. Soc. Chim., France 1967, pp. 40 to 46.
Vorsanger, Bull. Soc. Chim., France, 1968, pp. 964 to 970.

Primary Examiner—John D. Randolph
Attorney, Agent, or Firm—M. R. Chipaloski

[57] ABSTRACT

Compositions of matter are provided comprising a stable, non-vaporous monomeric methylene base selected from a 2-methylenethiazoline; a 2-methylenebenzothiazoline; a 2-methylenenaphthothiazoline; a 2-methylenebenzoselenazoline; and a 2-methylenenaphthoselenazoline. The compositions of the invention are prepared by reacting the parent 2-methyl quaternary salt with a non-hydroxylic base which removes a proton of the heterocyclic salt together with a proton acceptor which inhibits build-up of the hydro salt of the non-hydroxylic base, the reaction being conducted under anhydrous conditions in a non-hydroxylic liquid in which the heterocyclic quaternary salt is sufficiently insoluble to inhibit dimer formation. The compositions of the invention are employed in the preparation of methine dyes.

3 Claims, No Drawings

DYE INTERMEDIATES AND THEIR PREPARATION AND USE IN THE SYNTHESIS OF METHINE DYES

This invention relates to novel compositions of matter, and more particularly to compositions of dye intermediates. The invention also relates to the preparation of dye intermediates, and the use of such intermediates in the preparation of methine dyes.

Various 2-methylene bases derived from 2-methyl substituted heterocyclic nitrogen containing quaternary salts have been described in the literature. Certain of these compounds can be obtained without dimerization, such as the 2-methylene bases of the indolenines. See, for example, German Pat. No. 824,819, the examples of which employ the monomeric methylene base of indolenines. Although this patent appears to generically include 2-methylene bases of benzothiazoles, no instructions are given therein as to the method for obtaining 2-methylene- benzo- or naphthothiazoles. Also, certain substituted benzothiazolines form dimer-free compositions, such as those having the following formulas:

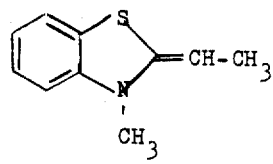

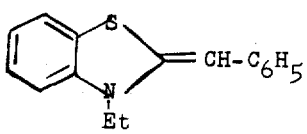

Stable, non-vaporous compositions of the 2-methylene substituted benzothiazoles, naphthothiazoles, benzoselenazoles and naphthoselenazoles have not been prepared heretofore. The preparation of the methylene base from 2,3-dimethylbenzothiazolium perchlorate was described by Konig and Meir (J.pr.Chem.109, 324(1925). While these authors believed that the methylene base was monomeric and had structure 1, (Ber., 72, 2107 (1939)), Mumm demonstrated by molecular weight determinations that it was in fact dimeric. Larive (Chimia, 15, 115 (1961))

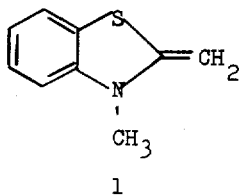

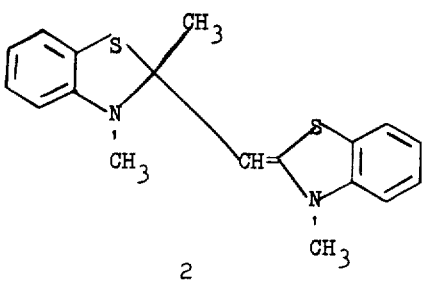

bases 3, 4 and 5. These compounds were shown to be reactive with a variety of intermediates to form cyanine and merocyanine dyes.

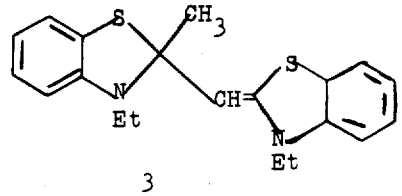

3

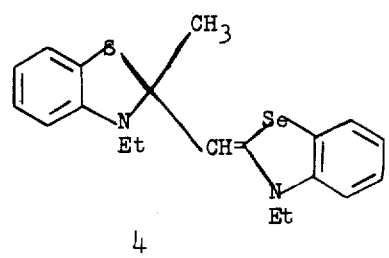

4

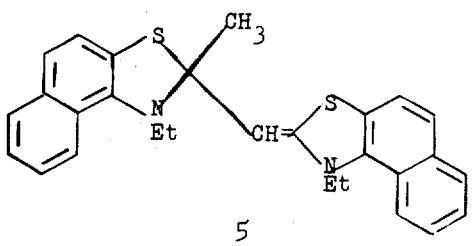

5

Larive et al in U.S. Pat. No. 2,921,067 refer to monomeric methylene bases in Column 4. However, the compounds employed by Larive et al were actually dimeric compounds and not the methylene bases of benzothiazole, benzoselenazole, naphthothiazole and naphthoselenazole, since monomeric methylene bases would not separate from the solution under the conditions described in Column 4 of Larive et al. There is no teaching by Larive et al as how to obtain monomeric determined that the correct structure of the methylene base was 2. In addition Larive described the preparation and determination of the structure of methylene methylene bases of the benzo or naphthothiazole or -selenazole type. Subsequently, as noted above, Larive, showed that the correct structure was the dimer.

Vorsanger in Bul.Chem.Soc. France 964 (1968) in making mass spectrograms from compositions of dimer formed by 2-methylene bases and the parent 2-methyl quaternary salt, indicated the dimer vaporized as the monomeric 2-methylene base. Such vaporized monomers would be totally unusable in the practical synthesis of methine dyes.

One object of this invention is to provide monomeric dye intermediates.

Another object of this invention is to provide a method for preparing monomeric dye intermediates.

Still another object of this invention is to provide a method for the preparation of methine dyes which features the use of certain monomeric dye intermediates.

Other objects of this invention will be apparent from the disclosure herein and the appended claims.

In accordance with one embodiment of this invention, a composition of matter is provided comprising a stable, nonvaporous monomeric methylene base of a 2-methylenethiazoline; a 2-methylenebenzothiazoline; a 2-methylenenaphthothiazoline; a 2-methylenebenzoselenazoline; or, a 2-methylenenaphthoselenazoline. The monomeric bases of this invention react substantially faster with other methine dye intermediates than their dimeric counterparts.

As used herein, the work "stable" denotes a nontransitory compound. "Stable" is intended to exclude "fleeting" compounds formed, for example, in the course of a chemical reaction. Hence, this invention excludes monomeric bases which might be formed as transitory intermediates when the dimer is reacted with the usual methine dye intermediates. The compositions of this invention can be stored, preferably at low temperature (e.g., 0°C.) and under anhydrous conditions.

The compositions of the invention are nonvaporous under normal, ambient pressures and generally are liquids or solids at temperatures of 35° to 40°C., or less. The compositions of the invention are in convenient form for reaction with methine dye intermediates.

The preferred compositions of the invention comprise monomeric methylene bases are substantially free of the dimer formed by the reacton of the methylene base with the parent methyl quaternary salt. The compositions of the invention can, however, contain dimer. Advantageously, any dimer is present in amounts less than 10%, and preferably less than 5.0% of the weight of the monomeric methylene base.

The preferred methylene bases of the invention have the following formula:

I.

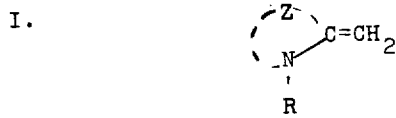

wherein Z represents the non-metallic atoms to complete a thiazoline nucleus, such as thiazoline, 4-methylthiazoline, 5-chlorothiazoline, 4-methoxythiazoline, etc.; a benzothiazoline nucleus, such as benzothiazoline, 4-chlorobenzoline, 5-chlorobenzothiazoline, 6-chlorobenzothiazoline, 7-chlorobenzothiazoline, 4-methylbenzothiazoline, 5-methylbenzothiazoline, 6-methylbenzothiazoline, 5-bromobenzothiazoline, 6-bromobenzothiazoline, 4-phenylbenzothiazoline, 5-phenylbenzothiazoline, 4-methoxybenzothiazoline, 5-methoxybenzothiazoline, 6-methoxybenzothiazoline, 5-iodobenzothiazoline, 6-iodobenzothiazoline, 4-ethoxybenzothiazoline, 5-ethoxybenzothiazoline, tetrahydrobenzothiazoline, 5,6-dimethoxybenzothiazoline, 5,6-dioxymethylenebenzothiazoline, etc.; a naphthothiazoline nucleus such as naphtho[1,2-d]thiazoline, naphtho[2,1-thiazoline, 5-methoxynaphtho[2,1-d]thiazoline, 5-ethoxynaphtho[2,3-d]thiazoline, 8-methoxynaphtho[1,2-d]thiazoline, 7-methoxynaphtho[1,2-d]-thiazoline, etc.; a benzoselenazoline nucleus such as benzoselenazoline, 5-chlorobenzoselenazoline, 5-methoxybenzoselenazoline, tetrahydro- benzoselenazoline, etc.; or a naphthoselenazoline nucleus, such as naphtho[1,2-d]selenazoline, naphtho[2,1-d]selenazoline, 5-chloronaphtho[2,1-d]selenazoline, 8-phenylnaphtho[2,1-d]-selenazoline, 7-methoxynaphtho[1,2-d]selenazoline, etc.; and, R represents an alkyl group, including substituted alkyl, (preferably a lower alkyl containing from 1 to 4 carbon atoms) e.g., methyl, ethyl, propyl, isopropyl, butyl, hexyl, cyclohexyl, decyl, dodecyl, etc., and substituted alkyl groups (preferably a substituted lower alkyl containing from 1 to 4 carbon atoms), such as an alkoxyalkyl group e.g., β-methoxyethyl, ω-butoxybutyl, etc., a carboxyalkyl group, e.g., β-carboxyethyl, ω-carboxybutyl, etc., a sulfoalkyl group, e.g., β-sulfoethyl, ω-sulfobutyl, etc., a sulfatoalkyl group, e.g., β-sulfatoethyl, ω-sulfatobutyl, etc., or an aralkyl group, e.g., benzyl, phenethyl, etc., and the like; or an aryl group, e.g., phenyl, tolyl, naphthyl, methoxyphenyl, chlorophenyl, etc. Some specific dimer-free monomeic methylene bases of the invention include the following: 3-methyl-2-methylenebenzothiazoline; 3-ethyl-2-methylenebenzo- selenazoline; 3-ethyl-2-methylene [1,2-d]naphthothiazoline; 3-(3-sulfobutyl)-2-methylenebenzothiazoline; 3-(2-carboxyethyl)-2-methylenebenzoselenazoline; 2-methylene-3-phenyl-benzothiazoline; 3-ethyl-2-methylene[2,1-d]-naphthothiazoline; and, 3-ethyl-2-methylenethiazoline.

In another embodiment of this invention, a method is provided for preparing monomeric methylene bases which comprises reacting a heterocyclic quaternary salt selected from a 2-methylthiazolium salt, a 2-methylbenzothiazolium salt, a 2-methylnaphthothiazolium salt, a 2-methylbenzoselenazolium salt and a 2-methylnaphthoselenazolium salt with a non-hydroxylic base which removes a proton of the heterocyclic quaternary salt to form monomeric 2-methylene base from the quaternary salt. together with a proton acceptor which inhibits build-up of the hydro salt of the non-hydroxylic base, the reaction being conducted under anhydrous conditions in a non-hydroxylic liquid in which the heterocyclic quaternary salt is sufficiently insoluble to prevent formation of a dimer by reaction between quaternary salt and methylene base. This process is particularly unobvious in view of the fact that related 2-methyl substituted quaternary salts, such as oxazoles, benzoxazoles and naphthoxazoles are not converted into dimer-free methylene bases by the processes of this invention.

The novel dye intermediate preparation in accordance with this invention is preferably initiated with a heterocyclic quaternary salt having the following formula:

II.

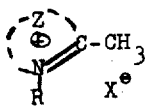

wherein Z and R have the meanings given above, and X represents any acid anion, such as chloride, bromide, iodide, thiocyanate, benzenesulfonate, perchlorate, p-toluenesulfonate, etc.

The process of the invention employs a non-hydroxylic base which removes a proton of the heterocyclic quaternary salt to form a corresponding monomeric methylene base. Any non-hydroxylic base which functions to remove the proton from the heterocyclic quaternary salt can be employed. Advantageously, the non-hydroxylic base has a pKa of at least 12. Non-hydroxylic bases which can be employed in the invention are 1,4-diazabicyclo-2,2,2-octane and tetramethylguanidine.

The reaction of the invention is conducted in the presence of a proton acceptor, which appears to facilitate the reaction by inhibiting or preventing build-up of the hydro salt of the non-hydroxylic base. Any suitable proton acceptor can be employed, such as sodium hydride or an organo lithium compound such as methyllithium or butyllithium.

The reaction of the invention is advantageously conducted in a non-hydroxylic liquid in which the heterocyclic quaternary salt is sufficiently insoluble to prevent formation of dimer by reaction between the quaternary salt and the methylene base. Suitable liquids include benzene and ligroine although various other materials can be utilized which are poor solvents for the quaternary salt.

The preparation of monomeric metylene base in accordance with the invention is conducted under anhydrous conditions. Advantageously, precautions are made to assure that all water is removed from the reaction mixture. Preferably the quaternary salt is added very slowly to the mixture of non-hydroxylic base, proton acceptor and non-hydroxylic liquid, while holding the mixture of non-hydroxylic base, proton acceptor and non-hydroxylic medium at 0°C. After addition of the quaternary salt, the temperature can be allowed to rise to room temperature, i.e., about 20°C. and the mixture stirred until all of the quaternary salt has dissolved and reacted. Preferably, the entire process is conducted under 30°C. The reaction can take several hours, such as 20 or more hours.

The concentrations of reactants employed in the process of the invention is not critical. Good results are obtained when substantially equal parts of non-hydroxylic base and non-hydroxylic liquid are utilized and the quaternary salt is added at a concentration of about up to 0.5 molar. The proton acceptor is advantageously added in an amount sufficient to prevent formation of the hydro salt of the strong base, e.g., in a concentration of up to about 0.5 molar and preferably at a slight molar excess over the concentration of the quaternary salt.

The success of the reaction of the invention is probably due to the ability of the excess strong base to rapidly remove the proton from the small amount of quaternary salt in the solution, with the proton acceptor preventing build-up of the hydro salt of the strong base.

In accordance with another embodiment of this invention, methine dyes are prepared by reacting a stable, non-vaporous monomeric methylene base selected from a 2-methylenethiazoline, a 2-methylenebenzothiazoline, a 2-methylenenaphthothiazoline, a 2-methylenebenzoselenazoline, and a 2-methylenenaphthoselenazoline with: an acetanilidovinyl salt of the type used in the synthesis of cyanine dyes, to obtain a cyanine dye; an N,N-disubstituted p-aminobenzaldehyde or an N,N-disubstituted p-aminocinnamaldehyde of the type used in the synthesis of styryl dyes, to obtain a styryl dye; or, an N,N-dimethylaminomethylene substituted acidic nucleus or an acetanilidovinyl derivative of an acidic nucleus of the type used in preparation of merocyanine dyes, to obtain a merocyanine dye. Preferably, the reaction is conducted in the absence of dimer formed by the monomeric methylene base and the parent 2-methyl substituted quaternary salt. Typical preferred acetanilidovinyl salts of the types used in the synthesis of cyanine dyes are represented by the following formula:

III.

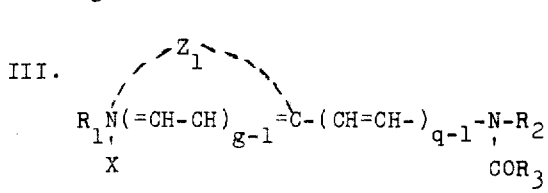

wherein $R_1$ and $X_1$ have a value given above for R and X; $g$ and $q$ each represents a positive integer of from 1 to 2; $R_2$ represents an aryl group of from 6–7 carbon atoms, e.g., phenyl, p-tolyl, etc., $R_3$ represents an alkyl group, such as referred to above; and, $Z_1$ represents the non-metallic atoms necessary to complete the same or different 5- to 6- membered heterocyclic nucleus such as used in cyanine dyes which may contain a second hetero atom such as oxygen, sulfur, selenium, or nitrogen, such as the following nuclei: a thiazole nucleus, e.g., thiazole, 4-methylthiazole, 4-phenylthiazole, 5-methylthiazole, 5-phenylthiazole, 4,5-dimethylthiazole, 4,5-diphenylthiazole, 4-(2-thienyl)thiazole, benzothiazole, 4-chlorobenzothiazole, 5-chlorobenzothiazole, 6-chlorobenzothiazole, 7-chlorobenzothiazole, 4-methylbenzothiazole, 5-methylbenzothiazole, 6-methylbenzothiazole, 5-bromobenzothiazole, 6-bromobenzothiazole, 5-phenylbenzothiazole, 6-phenylbenzothiazole, 4-methoxybenzothiazole, 5-methoxybenzothiazole, 6-methoxybenzothiazole, 5-iodobenzothiazole, 6-iodobenzothiazole, 4-ethoxybenzothiazole, 5-ethoxybenzothiazole, tetrahydrobenzothiazole, 5,6-dimethoxybenzothiazole, 5,6-dioxymethylenebenzothiazole, naphtho[2,1-d]thiazole, naphtho[1,2-d]thiazole, 5-methoxynaphtho[2,3-d]thiazole, 5-ethoxynaphtho[2,3-d]thiazole, 8-methoxynaphtho[2,3-d]thiazole, 7-methoxynaphtho[2,3-d]thiazole, 4'-methoxythianaphtheno-7',6', -4,5-thiazole, etc.; an oxazole nucleus, e.g., 4-methyloxazole, 5-methyloxazole, 4-phenyloxazole, 4,5-diphenyloxazole, 4-ethyloxazole, 4,5-dimethyloxazole, 5-phenyloxazole, benzoxazole, 5-chlorobenzoxazole, 5-methylbenzoxazole, 5-phenylbenzoxazole, 6-methylbenzoxazole, 5,6-dimethylbenzoxazole, 4,6-dimethylbenzoxazole, 5-methoxybenzoxazole, 5-ethoxybenzoxazole, 5-chlorobenzoxazole, 6-methoxybenzoxazole, naphtho[2,1-d]oxazole, naphtho[1,2-d]-oxazole, etc.; a selenazole nucleus e.g., 4-methylselenazole, 4-phenylselenazole, benzoselenazole, 5-chlorobenzoselenazole, 5l -methoxybenzoselenazole, tetrahydro- benzoselenazole, naphtho[ 2,1-d]selenazole, naphtho[ 1,2-d]selenazole, etc.; a thiazoline nucleus, e.g., thiazoline, 4-methylthiazoline, etc.; a pyridine nucleus, e.g., 2-pyridine, 5-methyl-2-pyridine, 4-pyridine, 3-methyl-4-pyridine, etc.; a quinoline nucleus, e.g., 2-quinoline, 3-methyl-2-quinoline, 5-ethyl-2-quinoline, 6-chloro-2-quinoline, 8-chloro-2-quinoline, 6-methoxy-2-quinoline, 8-ethoxy-2-quinoline, 4-quinoline, 6-methoxy-4-quinoline, 7-methyl-4-quinoline, 8-chloro-4-quinoline, 1-isoquinoline, 3,4-dihydro-1-isoquinoline, 3-isoquinoline, etc.; a 3,3-dialkylindolenine nucleus, e.g., 3,3-dimethylindolenine, 3,3,5-trimethylindolenine, etc.; and, an imidazole nucleus, e.g., 1-alkylimidazole, 1-alkyl-4-phenylimidazole, 1-alkyl-4,5-dimethylimidazole, benzimidazole, 1-alkylbenzimidazole, 1-aryl-5,6-dichlorobenzimidazole, 1-alkyl-1H-naphth[1,2-d]imidazole, 1-aryl-3H-naphth[1,2-d]imidazole, 1-alkyl-5-methoxy-1H-naphth-[1,2-d]imidazole, etc. This reaction is preferably carried out at moderate temperatures, such as 25°C., in a suitable solvent.

Styryl dyes are prepared by heating (preferably at about 25°C.) a mixture of a compound of Formula I (in which $R_2$ is metyl) with the appropriate N,N-disubstituted p-aminobenzaldehyde, or N,N-disubstituted p-aminocinnamaldehyde preferably in a suitable solvent and in the presence of a basic condensing agent.

Merocyanine dyes are prepared by heating (preferably at about 25°C.) a mixture of a compound of Formula I with a compound of the formula:

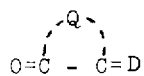

wherein D represents the group:

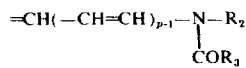

wherein $p$ represents a positive integer of from 1 to 2 and $R_2$ and $R_3$ are as previously defined; and, Q represents the non-metallic atoms necessary to complete a 5- or 6-membered acidic ketomethylene nucleus of the type used in merocyanine dyes typically containing a hetero atom selected from nitrogen, sulfur, selenium, and oxygen, such as a 2-pyrazoline-5-one nucleus, e.g., 3-methyl-1-phenyl-2-pyrazoline-5-one, 1-phenyl-2-pyrazolin-5-one, 1-(2-benzothiazolyl)-3-metyl-2-pyrazolin-5-one, etc., an isoxazolone nucleus, e.g., 3-phenyl-5(4H)-isoxazolone, 3-methyl-5(4H)-isoxazolone, etc.; an oxindole nucleus, e.g., 1-alkyl-2-oxindoles etc.; a 2,4,6-triketohexahydropyrimidine nucleus, e.g., a barbituric acid or a 2-thiobarbituric acid substituted in the 1- and 3-positions with an alkyl group (preferably having 1 to 4 carbon atoms) or an aryl group, e.g., methyl, ethyl, propyl, isopropyl, heptyl, cycohexyl, β-methoxyethyl, phenyl, p-chlorophenyl, naphthyl, etc.; a rhodanine nucleus (i.e., 2-thio-2,4-thiazolidinedione series), such as rhodanine, 3-alkylrhodanines, e.g., 3-ethylrhodanine, 3-allylrhodanine, etc., 3-carboxyalkylrhodanines, e.g., 3-(2-carboxyethyl)rhodanine, 3-(4-carboxybutyl)rhodanine, etc., 3-sulfoalkylrhodanines, e.g., 3-(2-sulfoethyl)rhodanine, 3-(3-sulfopropyl)rhodanine, 3-(4-sulfobutyl)rhodanine, etc., or 3-arylrhodanines, e.g., 3-phenylrhodanine, etc., etc.; a 2(3H)-imidazo[1,2-a]pyridone nucleus; a 5,7-dioxo-6,7-dihydro-5-thiazolo[3,2-a]pyrimidine nucleus, e.g., 5,7-dioxo-3-phenyl-6,7-dihydro-5-thiazolo[3,2-a]-pyrimidine, etc.; a 2-thio-2,4-oxazolidinedione nucleus (i.e., those of the 2-thio-2,4(3H,5H)-oxazoledione series) e.g., 3-ethyl-2-thio-2,4-oxazolidinedione, 3-(2-sulfoethyl)-2-thio-2,4-oxazolidinedione, 3-(4-sulfobutyl)-2-thio-2,4-oxazolidinedione, 3-(3-carboxypropyl)-2-thio-2,4-oxazolidinedione, etc.; a thianaphthenone nucleus e.g., 3-(2H)-thianaphthenone, etc.; a 2-thio-2,5-thiazolidinedione nucleus (i.e., the 2-thio-2,5-(3H,4H)-thiazoledione series), e.g., 3-ethyl-2-thio-2,5-thiazolidinedione, etc.; a 2,4-thiazolidinedione nucleus, e.g., 2,4-thiazolidinedione, 3-ethyl-2,4-thiazolidinedione, 3-phenyl-2,4-thiazolidinedione, 3-α-naphthyl-2,4-thiazolidinedione, etc.; a thiazolidinone nucleus, e.g., 4-thiazolidinone, 3-ethyl-4-thiazolidinone, 3-phenyl-4-thiazolidinone, 3-α-naphthyl-4-thiazolidinone, etc.; a 2-thiazolin-4-one nucleus, e.g., 2-ethylmercapto-2-thiazolin-4-one, 2-alkylphenylamino-2-thiazolin-4-one, 2-diphenylamino-2-thiazolin-4-one, etc.; a 2-imino-4-oxazolidinone (i.e., pseudohydantoin) nucleus; a 2,4-imidazolidinedione (hydantoin) nucleus, e.g., 2,4-imidazolidinedione, 3-ethyl-2,4-imidazolidinedione, 3-phenyl-2,4-imidazolidinedione, 3-α-naphthy-2,4-imidazolidinedione, 1,3-diethyl-2,4-imidazolidinedione, 1-ethyl-3-phenyl-2,4-imidazolidinedione, 1-ethyl-3-α-naphthyl-2,4-imidazolidinedione, 1,3-diphenyl-2,4-imidazolidinedione, etc.; a 2-thio-2,4-imidazolidinedione (i.e., 2-thiohydantoin) nucleus, e.g., 2-thio-2,4-imidazolidinedione, 3-ethyl-2-thio-2,4-imidazolidinedione, 3-(4-sulfobutyl)-2-thio-2,4-imidazolidinedione, 3-(2-carboxyethyl)-2-thio-2,4-imidazolidinedione, 3-phenyl-2-thio-2,4-imidazolidinedione, 3-α-naphthyl-2-thio-2,4-imidazolidinedione, 1,3-diethyl-2-thio-2,4-imidazolidinedione, 1-ethyl-3-phenyl-2-thio-2,4-imidazolidinedione, 1-ethyl-3 -α-naphthyl-2-thio-2,4-imidazolidinedione, 1,3-diphenyl-2-thio-2,4-imidazolidinedione, etc.; a 2-imidazolin-5-one nucleus, e.g., 2-propylmercapto-2-imidazolin-5-one, etc.; etc.

The monomeric methylene bases in accordance with this invention can be employed immediately after preparation for the formation of methine dyes, or can be stored, preferably at 0°C. or dry ice temperature.

The following examples are included for a further understanding of the invention.

EXAMPLE 1

3-Methyl-2-methylenebenzothiazoline

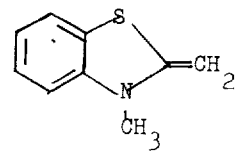

To a mixture of ligroine (b.p. = 63°–75°) (75 ml.) and tetramethylguanidine (75 ml.) dried over sodium hydride is added 0.06 mol. of sodium hydride which had been previously washed with ligroine to remove any oil present. The mixture is cooled in an ice bath under nitrogen and 2,3-dimethylbenzothiazolium p-toluenesulfonate, 13.4 g. (0.0400 mol.) is added, with stirring, in small portions over three hours. After all the solid is added, the mixture is stirred for 20 hours at room temperature. The mixture is filtered through filter cell to remove the sodium p-toluenesulfonate. After removal of the ligroine and tetramethylguanidine by vacuum distillation, the remaining yellow oil is distilled under vacuum to give 4.7 g. (72%) of a clear liquid b.p. 90°–91° (0.07 mm. Hg.). The product is stable at dry-ice temperature.

EXAMPLE 2

3-Ethyl-2-methylenebenzothiazoline

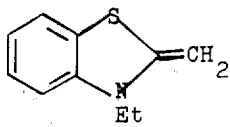

To a mixture of benzene (110 ml.) and tetramethylguanidine (40 ml.) which had been dried over sodium hydride is added 0.06 mol. of sodium hydride which had been previously washed with benzene to remove any oil present. The mixture is cooled in an ice bath under nitrogen and 3-ethyl-2-methylbenzothiazolium p-toluenesulfonate, 13.9 g. (0.0400 mol.) is added in small portions, with stirring, over one hour. After all the solid is added, the mixture is stirred at ice-bath temperature for one hour and then at room temperature for an additional 20 hours. The reaction mixture is then filtered through filter cell to remove the sodium p-toluenesulfonate. After removal of the benzene and tetramethylguanidine by vacuum distillation, the remaining yellow oil is distilled through a 6-inch Vigreux column under vacuum to give 5.9 g. (83%) of a clear liquid b.p. 110° (0.05 mm. Hg.). The nmr. spectrum of the liquid taken immediately after distillation gives the following nmr. values: 7.1—6.2 (m,4 aromatic H) 3.9 (m,2, $CH_2 = C<$), 3.31 ($q$,2,J=7H$_z$, —$CH_2$—), 0.92 ($t$,3, J=7Hz, —$CH_3$). The product is stable for several weeks at dry ice temperature. When the above example is repeated except employing anhydro-3-(3-sulfobutyl)-2-methylbenzothiazolium hydroxide there is obtained in similar yield 3-(3-sulfobutyl)-2-methylenebenzothiazoline which can be removed from the reaction mixture by crystallization.

EXAMPLE 3

3-Ethyl-2-methylenebenzoselenazoline

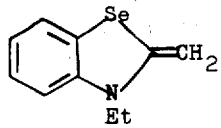

To a mixture of ligroine (b.p. 63°–75°) (75 ml.) and tetramethylguanidine (75 ml.) dried over sodium hydride is added 0.06 mol. of sodium hydride which had been previously washed to remove any oil present. The mixture is cooled in an ice bath under nitrogen and 3-ethyl-2-methyl-benzoselenazolinium p-toluenesulfonate, 15.7 g. (0.04 mol.) is added in small portions over three hours to the stirred mixture. The mixture is stirred an additional 20 hours after addition at room temperature. The mixture is then filtered through filter cell. After removal of the ligroine and tetramethylguanidine by vacuum distillation, the remaining dark yellow liquid is vacuum distilled to give 5.2 g. (59%) of liquid b.p. 105°(0.03 mm. Hg.) which solidified on standing m.p. 23°–25°. An nmr spectrum taken on the liquid immediately after distillation gives the following nmr values: 7.1–6.1 (m,4 aromatic H), 4.1 (m,2, $CH_2=C<$), 3.8 ($q$,2, J=7Hz, —$CH_2$—), 0.88 ($t$, J=7Hz, —$CH_3$). The product is stable at dry ice temperature.

EXAMPLE 4

3-Ethyl-2-methylene[1,2-d]naphthothiazoline

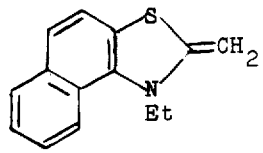

To a mixture of ligroine (b.p. 63°–75°) (75 ml.) and tetramethylguanidine (75 ml.) which had been dried over sodium hydride is added 0.06 mol. of sodium hydride which had been previously washed to remove any oil present. The mixture is cooled in an ice bath under nitrogen and 3-ethyl-2-methyl[1,2-d]naphthothiazolium p-toluenesulfonate 16.09 g. (0.04 mol.) is added in small portions, with stirring, over three hours. The mixture is stirred an additional 20 hours after addition at room temperature. The mixture is filtered through filter cell to remove the sodium p-toluenesulfonate. The benzene is then distilled from the solution. An nmr. spectrum obtained of the tetramethylguanidine solution indicated that the monomeric methylene base had formed exclusively. Removal of the tetramethylguanidine in an attempted distillation of the product resulted in extensive decomposition. The product is stable in tetramethylguanidine at room temperature. The nmr. values are as follows: 8.0-7,1 (m,6, aromatic H), 3.9 (m,2, $CH_2=C<$), 3.91 ($q$,J=7H$_z$ , —$CH_2$—), 1.32 ($t$,3,J=7Hz, —$CH_3$).

EXAMPLE 5

Reaction of 3-ethyl-2-(3-ethylbenzothiazolylidenemethyl)-2-methylbenzothiazoline with 5-(N,N-dimethylaminomethylene)-1,3-diethyl-2-thiobarbituric acid

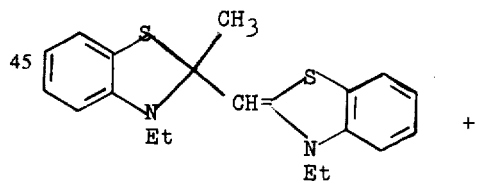

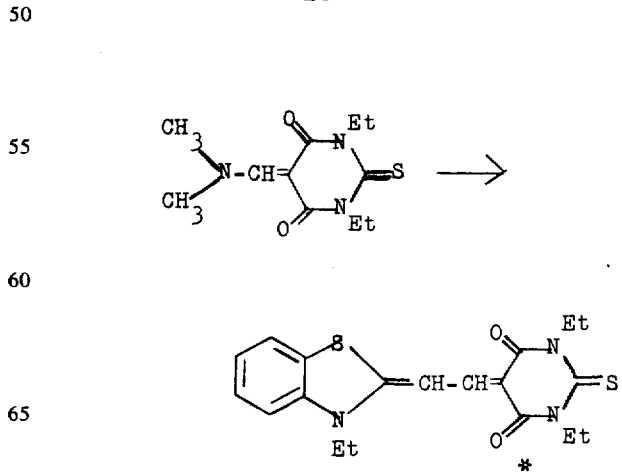

*L. Brooker, U.S. Pat. No. 2,170,807 (8/29/39).

To 2.58 ml. of a solution of 5-(N,N-dimethylaminomethylene)-1,3-diethyl-2-thiobarbituric acid ($1.7 \times 10^{-2}$M) and triethylamine ($1.7 \times 0.0^{-1}$M) in anhydrous acetonitrile is added 0.071 ml. of a solution of 3-ethyl-2-(3-ethylbenzothiazolylidenemethyl)-2-methylbenzothiazoline ($3.2 \times 10^{-4}$M) in anhydrous acetonitrile. The rate of formation of merocyanine dye at 25° is followed by observing the absorption of the dye at 496 nm. as a function of time using a recording spectrophotometer. The reaction is 50 percent complete in 51 minutes.

EXAMPLE 6

Reaction of 3-ethyl-2-methylenebenzothiazoline with 5-(N,N-dimethylaminomethylene)-1,3-diethyl-2-thiobarbituric acid

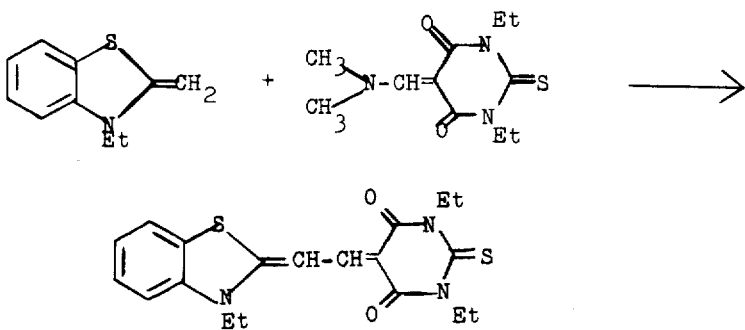

To 2.58 ml. of a solution of 5-(N,N-dimethylaminomethylene)-1,3-diethyl-2-thiobarbituric acid ($1.7 \times 10^{-2}$M) in anhydrous acetonitrile is added 0.071 ml. of a solution of 3-ethyl-2-methylenebenzothiazoline ($5.3 \times 10^{-4}$M) and tetramethylguanidine ($8.7 \times 10^{-3}$M) in anhydrous acetonitrile. The rate of formation of merocyanine dye at 25° is followed by observing the absorption of the dye at 496 nm. as a function of time using a recording spectrophotometer. The reaction is 50 percent complete in 2.2 minutes. In a similar manner, the intermediate obtained in Example 2 above can be reacted with a 2-β-acetanilidovinyl-3-methylbenzothiazolium iodide by refluxing in acetonitrile to obtain a cyanine dye; and, a styryl dye can be obtained by reacting the intermediate obtained in Example 2 with N,N-dimethyl-p-aminobenzaldehyde (or N,N-diethyl-p-aminocinnamaldehyde).

The invention has been described in detail with particular reference to preferred embodiments thereof, but, it will be understood that variations and modifications can be effected within the spirit and scope of the invention.

I claim:

1. The method of preparing a monomeric methylene base which comprises adding up to 0.5 molar of a heterocyclic quaternary salt selected from the group consisting of a 2-methylthiazolium salt, a 2-methylbenzothiazolium salt, a 2-methylnaphthothiazolium salt, a 2-methylbenzoselenazolium salt, and a 2-methylnaphthoselenazolium salt to a mixture comprising one part tetramethylguanidine and one part of a liquid selected from benzene and ligroine, the temperature of said mixture being maintained at approximately 0°C. during the addition of said heterocyclic base, said reaction being conducted under anhydrous conditions and in the presence of sodium hydride in a concentration of up to about 0.5 molar.

2. The method of preparing 3-methyl-2-methylenebenzothiazoline which comprises adding 13.4 g. 2,3-dimethylbenzothiazolium p-toluenesulfonate to an ice bath solution essentially consisting of 75 ml. tetramethyl guanidine and 75 ml. ligroine containing about 0.06 mole sodium hydride, said reaction being conducted under anhydrous conditions and with stirring, the 2,3-dimethylbenzothiazolium p-toluenesulfonate being added slowly to the reaction solution over a period of 3 hours, and stirring the reaction mixture thereafter for about 20 hours at about 20°C.

3. The method of preparing a monomeric methylene base which comprises reacting a heterocyclic quaternary salt selected from the group consisting of a 2-methylthiazolium salt, a 2-methylbenzothiazolium salt, a 2-methylnaphthothiazolium salt, a 2-methylbenzoselenazolium and a 2-methylnaphthoselenazolium salt, with:

1. a non-hydroxylic base selected from the group consisting of 1,4-diazabicyclo-2,2,2-octane and tetramethyl guanidine to convert said heterocyclic quaternary salt to the corresponding methylene base, and
2. a proton acceptor which prevents formation of the hydro salt of the non-hydroxylic base;

said reaction being conducted under anhydrous conditions in a non-hydroxylic liquid in which said heterocyclic quaternary salt is sufficiently insoluble to prevent formation of dimer by reaction between the quaternary salt and the methylene base.

* * * * *